United States Patent [19]

Elliott

[11] Patent Number: 5,720,783
[45] Date of Patent: Feb. 24, 1998

[54] MANUFACTURE OF FERROUS PICRATE AND ADDITIVES CONTAINING SAME

[76] Inventor: Alan Frederick Elliott, 334 Dorcas Street, South Melbourne, Australia, Victoria 3205

[21] Appl. No.: 553,400

[22] PCT Filed: May 19, 1994

[86] PCT No.: PCT/AU94/00259

§ 371 Date: May 17, 1996

§ 102(e) Date: May 17, 1996

[87] PCT Pub. No.: WO94/26689

PCT Pub. Date: Nov. 24, 1994

[30] Foreign Application Priority Data

May 19, 1993 [AU] Australia .................. PL8875

[51] Int. Cl.$^6$ .................................................. C10L 1/22
[52] U.S. Cl. ................................. 44/323; 44/367; 556/150
[58] Field of Search ................... 44/323, 367; 556/150

[56] References Cited

U.S. PATENT DOCUMENTS

| | | | |
|---|---|---|---|
| 2,506,539 | 5/1950 | Boardman | 44/367 |
| 3,282,858 | 11/1966 | Simmons | 44/367 |
| 4,073,626 | 2/1978 | Simmons | 44/367 |
| 4,099,930 | 7/1978 | Webb | 44/354 |
| 4,129,421 | 12/1978 | Webb | 44/354 |
| 4,265,639 | 5/1981 | Scholtz | 44/367 |
| 4,424,063 | 1/1984 | Hart | 44/354 |
| 5,087,268 | 2/1992 | Parish | 44/367 |

FOREIGN PATENT DOCUMENTS 624964  9/1991  Australia.

*Primary Examiner*—Stephen Kalafut
*Assistant Examiner*—Cephia D. Toomer
*Attorney, Agent, or Firm*—Thompson E. Fehr

[57] ABSTRACT

A process for preparing ferrous picrate is disclosed. The process includes the step of reacting under substantially non-oxidising conditions ferrous carbonate substantially free from ferric compounds with a substantially water-free solution of picric acid in a solvent medium to produce a solution of ferric picrate. The solvent medium is selected from aromatic hydrocarbon solvents, mixtures of aromatic hydrocarbon solvents, straight- or branched-chain aliphatic alcohols, mixtures of straight or branched-chain aliphatic alcohols, and mixtures of straight- or branched-chain aliphatic alcohols and aromatic hydrocarbon solvents. The reaction is preferably carried out under a continuously maintained inert atmosphere and at a temperature between 10° C. and 120° C.

21 Claims, No Drawings

MANUFACTURE OF FERROUS PICRATE AND ADDITIVES CONTAINING SAME

This application is a 371 of PCT/AU94/00259, filed May 19, 1994.

BACKGROUND OF THE INVENTION

The present invention relates to the manufacture of ferrous picrate.

It has been suggested that the addition of ferrous picrate to carbonaceous fuel results in improvement to the combustion of the fuel. Both ferrous picrate and picric acid are to some extent explosive when in the dry state, necessitating precautions in their use and transport. Ferrous picrate in the dry state is also readily oxidised to ferric picrate in air. Ferric compounds are ineffective as combustion improvers.

In Australian Patent No. 621243 there is disclosed a process for preparing ferrous picrate comprising reacting picric acid in solution in a straight- or branched-chain aliphatic alcohol with iron carbonyl at a temperature between 10° C. and 120° C. Also disclosed is a liquid additive comprising ferrous picrate prepared by the process described, picric acid, an aromatic solvent, and a straight- or branched-chain aliphatic alcohol.

In Australian Patent No. 624964 there is disclosed a process for preparing ferrous picrate comprising reacting under a continuously maintained inert atmosphere an aqueous solution of a ferrous salt with an alkali hydroxide to produce a ferrous hydroxide precipitate, removing water and by-products from the ferrous hydroxide, adding the ferrous hydroxide and a straight or branched-chain aliphatic alcohol to a water-free solution of picric acid in an aromatic solvent, and removing any insoluble material from the solution. Also disclosed is a liquid additive comprising ferrous picrate prepared by a process as described, an aromatic solvent, an aromatic nitro compound and a straight- or branched-chain aliphatic alcohol.

In Example 5 of U.S. Pat. No. 3,282,858, a method of manufacture of ferrous picrate is disclosed which comprises reacting ferrous sulphate with sodium carbonate to produce a ferrous carbonate precepitate which is then dissolved in alcohol and reacted with picric acid to produce ferrous picrate. The ferrous picrate crystals are separated from the liquid in which they are made, and taken up in solvents to provide a fuel additive. No attempt is made to exclude oxygen from the ferrous carbonate solution or the solid ferrous picrate, but hydroquinone is added to the reaction mixture to minimise the oxidation of ferrous compounds.

SUMMARY OF THE INVENTION

One object of the present invention is to provide in one embodiment a process for preparing ferrous picrate for subsequent use as a fuel additive whereby the use of materials in a hazardous state is avoided, and whereby the presence of ferric compounds is minimised.

Accordingly, in one embodiment the present invention provides a process for preparing ferrous picrate comprising reacting under an inert atmosphere ferrous carbonate substantially free from ferric compounds with a solution of substantially water-free picric acid in a solvent medium selected from an aromatic hydrocarbon solvent, a mixture of aromatic hydrocarbon solvents, a straight- or branched-chain aliphatic alcohol, mixtures of straight- and/or branched-chain aliphatic alcohols, and a mixture of straight- and/or branched-chain aliphatic alcohols with aromatic hydrocarbon solvents, to produce a solution of ferrous picrate.

In another embodiment, the present invention provides a process for preparing ferrous picrate comprising reacting under an inert atmosphere ferrous carbonate substantially free from ferric compounds with a substantially water-free solution of picric acid in a solvent medium selected from an aromatic hydrocarbon solvent, a mixture of aromatic hydrocarbon solvents, a straight- or a branched-chain aliphatic alcohol, a mixture of straight- and/or branched-chain aliphatic alcohols, and a mixture of straight- and/or branched-chain aliphatic alcohols with aromatic hydrocarbon solvents and at a temperature between 10° C. and 120° C., to produce a solution of ferrous picrate.

We have now surprisingly found in one particularly preferred embodiment of the invention that by reacting ferrous carbonate which is substantially free from ferric compounds with picric add under an inert atmosphere, without adding hydroquinone, and maintaining the ferrous picrate and the picric acid always in solution, we can obtain a ferrous picrate product that is more effective in promoting the complete combustion of carbonaceous fuel than is the ferrous picrate product produced by the process of Example 5 of U.S. Pat. No. 3,282,858. In addition, hazards which would arise from dry ferrous picrate and dry picric acid are avoided.

The process of the present invention also provides a viable alternative to the process disclosed in, for example, Australian Patent No. 621243 when a source of iron carbonyl is otherwise unavailable, or for health reasons the use of iron carbonyl, which is a toxic compound, is considered unsafe.

The reaction is preferably carried out under a continuously maintained inert atmosphere eg. nitrogen to achieve a substantially non-oxidising reaction condition.

The ferrous carbonate is preferably prepared by reacting in solution ferrous sulphate with sodium carbonate and removing aqueous liquid under a continuously maintained inert atmosphere. The preferred inert atmosphere is an atmosphere of nitrogen.

The reaction between ferrous carbonate and picric acid is preferably conducted at a temperature between 30° C. and the boiling point of the solvent medium. More preferably the reaction between ferrous carbonate and picric acid is conducted at a temperature between 60° C. and the boiling point of the solvent medium.

Alternatively, the reaction between ferrous carbonate and picric acid may be conducted at a temperature between 10° C. and 120° C., and more preferably between 60° C. and 100° C.

The aliphatic alcohols are preferably straight- or branched-chain $C_1$ to $C_{12}$ aliphatic alcohols. More preferred aliphatic alcohols are straight- or branched-chain $C_2$, $C_3$ or $C_4$ aliphatic alcohols. Examples of suitable alcohols include isopropanol, n.butanol and iso-octanol.

The preferred aromatic hydrocarbon solvents are alkylbenzenes or mixtures thereof. Examples include toluene, xylene, or mixtures of toluene and xylene. Another suitable aromatic hydrocarbon solvent is marketed under the trade name Solvesso (a trade mark of Exxon Corporation), which comprises a mixture of commercial aromatic hydrocarbon fractions.

The present invention also provides a liquid additive for addition to carbonaceous fuel comprising a ferrous picrate solution produced as herein described, an aromatic solvent, and a straight- or branched-chain aliphatic alcohol.

Picric acid may also be added to the liquid additive if it is considered that the ferrous picrate solution does not itself contain sufficient free picric acid.

DETAILED DESCRIPTION OF PREFERRED EMBODIMENT

The present invention will now be described with reference to the following non-limiting examples.

EXAMPLE 1

Hydrated ferrous sulphate (2.5 g) was dissolved in 100 ml of water at room temperature in a 250 ml erlenmeyer flask and sparged with nitrogen. About 1 g of "Supercel" (trade mark) filter aid was added to the solution followed by a 5% solution of sodium carbonate until the liquid became alkaline. The liquid was then heated to about 80° C. whilst maintaining the nitrogen blanket.

The resulting slurry was filtered by suction on a glass fibre filter and the precipitate washed with hot water until the washings were neutral whilst maintaining a continuous nitrogen blanket. The precipitate was washed twice with isopropanol and then once with n.butanol to remove water, maintaining a blanket of nitrogen.

Wet picric acid containing 9 g picric acid on a dry basis and 9 g of water was added to 500 ml of xylene in a separating funnel and stirred until the picric acid has dissolved. The liquid was allowed to stand until the aqueous phase had settled to the bottom. The aqueous phase was run off and discarded. The solution of picric acid in xylene was then added to 400 ml of butanol in a 2l flask and the air above the liquid was replaced with nitrogen. The filter pad was quickly transferred to the flask and the resulting mixture stirred and heated to 80° C. while maintaining the nitrogen blanket. The mixture became intensely green as ferrous picrate formed. After about 4 hours when the reaction was complete the nitrogen blanket was discontinued and the mixture was filtered on a glass fibre filter and washed briefly with n.butanol. The filtrate was retained and made up to 1l with n.butanol. Analysis revealed that the resulting solution contained 480 mg/l of ferrous iron.

EXAMPLE 2

A fuel additive of the following composition for addition to diesel fuel was formulated from the above solution.

| | |
|---|---|
| Ferrous picrate | 0.9 g |
| Picric acid | 1.0 g |
| n.Butanol | 110 ml |
| Xylene | 890 ml |

While it has been convenient to describe the invention herein in relation to particularly preferred embodiments, it is to be appreciated that other constructions and arrangements are also considered as falling within the scope of the invention. Various modifications, alterations, variations and/or additions to the constructions and arrangements described herein are also considered as falling within the scope and ambit of the present invention.

I claim:

1. A process for preparing ferrous picrate comprising reacting under an inert atmosphere ferrous carbonate substantially free from ferric compounds with a substantially water-free solution of picric acid in a solvent medium selected from an aromatic hydrocarbon solvent, a mixture of aromatic hydrocarbon solvents, a straight- or a branched-chain aliphatic alcohol, a mixture of straight-chain aliphatic alcohols, a mixture of branched-chain aliphatic alcohols, a mixture of straight- and branched-chain aliphatic alcohols, a mixture of straight-chain aliphatic alcohols with aromatic hydrocarbon solvents, a mixture of branched-chain aliphatic alcohols with aromatic hydrocarbon solvents, and a mixture of straight- and branched-chain aliphatic alcohols with aromatic hydrocarbon solvents, to produce a solution of ferrous picrate.

2. A process according to claim 1, wherein the inert atmosphere is continuously maintained during said reaction.

3. A process according to claim 1, wherein the ferrous carbonate is produced by reacting in solution under an inert atmosphere ferrous sulphate with sodium carbonate and in the absence of any added hydroquinone.

4. A process according to claim 2, wherein the inert atmosphere is an atmosphere of nitrogen.

5. A process according to claim 3, wherein the inert atmosphere is an atmosphere of nitrogen.

6. A process according to claim 1, wherein the reaction between ferrous carbonate and picric acid is conducted at a temperature between 30° C. and the boiling point of the solvent medium.

7. A process according to claim 2, wherein the reaction between ferrous carbonate and picric acid is conducted at a temperature between 30° C. and the boiling point of the solvent medium.

8. A process according to claim 3, wherein the reaction between ferrous carbonate and picric acid is conducted at a temperature between 30° C. and the boiling point of the solvent medium.

9. A process according to claim 6, wherein the reaction between ferrous carbonate and picric acid is conducted at a temperature between 60° C. and the boiling point of the solvent medium.

10. A process according to claim 7, wherein the reaction between ferrous carbonate and picric acid is conducted at a temperature between 60° C. and the boiling point of the solvent medium.

11. A process according to claim 8, wherein the reaction between ferrous carbonate and picric acid is conducted at a temperature between 60° C. and the boiling point of the solvent medium.

12. A process according to claim 1, wherein the aliphatic alcohol is a straight- or branched-chain $C_1$ to $C_{12}$ aliphatic alcohol.

13. A process according to claim 12, wherein the aliphatic alcohol is a straight- or branched-chain $C_2$, $C_3$ or $C_4$ aliphatic alcohol.

14. A process according to claim 1, wherein the aromatic hydrocarbon solvent is selected from alkylbenzenes, mixtures thereof and commercial aromatic hydrocarbon fractions.

15. A process according to claim 14, wherein the alkylbenzene is selected from toluene, xylene and mixtures thereof.

16. A process according to claim 1, wherein said reaction is conducted in the absence of any added hydroquinone.

17. A process for preparing ferrous picrate comprising reacting under an inert atmosphere ferrous carbonate substantially free from ferric compounds with a substantially water-free solution of picric acid in a solvent medium selected from an aromatic hydrocarbon solvent, a mixture of aromatic hydrocarbon solvents, a straight- or a branched-chain aliphatic alcohol, a mixture of straight-chain aliphatic alcohols, a mixture of branched-chain aliphatic alcohols, a mixture of straight- and branched-chain aliphatic alcohols, a mixture of straight-chain aliphatic alcohols with aromatic hydrocarbon solvents, a mixture of branched-chain aliphatic alcohols with aromatic hydrocarbon solvents, and mixture of straight- and branched-chain aliphatic alcohols with aromatic hydrocarbon solvents and at a temperature between 10° C. and 120° C., to produce a solution of ferrous picrate.

18. A process according to claim 17, wherein said temperature is between 60° C. and 100° C.

19. A liquid additive for addition to carbonaceous fuel comprising a ferrous picrate solution produced by a process comprising reacting under an inert atmosphere ferrous carbonate substantially free from ferric compounds with a substantially water-free solution of picric acid in a solvent medium selected from aromatic hydrocarbon solvents, mixtures of aromatic hydrocarbon solvents, straight- or branched-chain aliphatic alcohols, mixtures of straight-chain aliphatic alcohols, mixtures of branched-chain aliphatic alcohols, mixtures of straight- and branched-chain aliphatic alcohols, mixtures of straight-chain aliphatic alcohols and aromatic hydrocarbon solvents, mixtures of branched-chain aliphatic alcohols with aromatic hydrocarbon solvents, and mixtures of straight- and branched-chain aliphatic alcohols with aromatic hydrocarbon solvents, to produce a solution of ferrous picrate, an aromatic hydrocarbon solvent, and a solvent medium selected from a straight-chain aliphatic alcohol, a branched-chain aliphatic alcohol, and a mixture of straight- and branched-chain aliphatic alcohols.

20. A liquid additive according to claim 19, further comprising added picric acid.

21. A liquid additive according to claim 19, wherein said reaction is conducted in the absence of any added hydroquinone.

* * * * *